United States Patent [19]

Liang et al.

[11] Patent Number: 4,600,710

[45] Date of Patent: Jul. 15, 1986

[54] β-ADRENERGIC RECEPTOR AGONIST ALKYLAMINOALKYL PYRIDINEMETHANOL DERIVATIVES

[75] Inventors: Chi-Dean Liang, Glenview; Gerald M. Walsh, Lindenhurst, both of Ill.

[73] Assignee: G. D. Searle & Co., Skokie, Ill.

[21] Appl. No.: 711,899

[22] Filed: Mar. 14, 1985

[51] Int. Cl.$^4$ .................. C07D 213/38; A61K 31/44
[52] U.S. Cl. ..................................... 514/357; 546/334
[58] Field of Search ........................ 546/334; 514/357

[56] References Cited

PUBLICATIONS

Chemical Abstracts 77: 61749(n) (1972).
Chemical Abstracts 56: 2415(e).
Chemical Abstracts 45: 7571(b).

Primary Examiner—Henry R. Jiles
Assistant Examiner—Dale A. Bjorkman
Attorney, Agent, or Firm—Steven M. Odre

[57] ABSTRACT

β-Adrenergic receptor site activation by novel pyridinemethanol derivatives and pharmaceutical compositions and methods of use thereof are described.

11 Claims, No Drawings

β-ADRENERGIC RECEPTOR AGONIST ALKYLAMINOALKYL PYRIDINEMETHANOL DERIVATIVES

BACKGROUND OF THE INVENTION

The present invention relates generally to novel pyridinemethanol derivatives and the β-adrenergic receptor agonist activity thereof.

More particularly, the present invention is directed to the compound α-[(1-methylethylamino)methyl]-3-pyridinemethanol of formula I

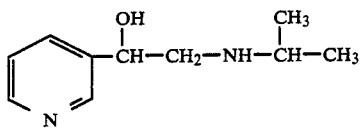

which has been found to possess valuable long-acting β-adrenergic agonist activity.

Various 3-pyridinemethanol derivatives have previously been described in the literature. For example, α-[ethylamino(methyl)]-,α[(methylamino)methyl]- and α-[(propylamino)methyl]-pyridinemethanol derivatives having potential circulatory system action are described by F. Zymalkowski and F. Koppe [Chem. Abs., 56, 2415(e)]. Likewise, α-[diethylaminomethyl]-3-pyridinemethanol is described in Chem. Abs. 45, 7571(b) without mention of any pharmacological properties.

These publications do not describe the preferred compound of the present invention or the β-receptor agonist activity thereof.

SUMMARY OF THE INVENTION

It is, therefore, a primary object of the present invention to afford α-[(1-methylethylamino)methyl]-3-pyridinemethanol and acid addition salts thereof.

It is a further object of the present invention to provide methods for promoting beneficial cardiovascular and/or respiratory effects in mammals in need thereof by the administration of preselected dosages of the compound of the present invention or pharmaceutically acceptable salts thereof in appropriate nontoxic pharmaceutical dosage unit forms or compositions.

A still further object of the present invention is to provide dosage unit forms adapted for, e.g., oral, rectal, parenteral, etc. administration and useful in the treatment, management and mitigation of cardiovascular, cardiopulmonary, or respiratory conditions or disorders.

DETAILED DESCRIPTION OF THE PREFERRED EMBODIMENTS

These and other similar objects, advantages and features are accomplished according to the products, compositions and methods of the invention comprised of α-[(1-methylethylamino)methyl]-3-pyridinemethanol of the formula

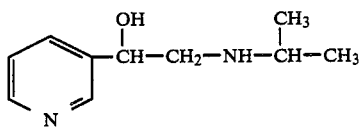

or pharmaceutically acceptable salts thereof.

As used herein, the expression "pharmaceutically acceptable salts" is intended to include those salts capable of being formed with the present compound in accordance with the invention without materially altering the chemical structure or pharmacological properties thereof. Such salts include inorganic and organic acid addition salts, such as hydrochloric, hydrobromic, phosphoric, citric, maleic, oxalic, etc. with the oxalate salt being presently preferred.

As a consequence of the β-receptor agonist activity of the 3-pyridinemethanol derivative of the present invention, it is suitable for use in various ultimate therapeutic applications involving organ systems in which stimulation of β-adrenergic receptor sites may be important in the prevention, treatment, management, alleviation or reversal of such conditions or disorders. As a long-acting β-adrenergic receptor agonist, the compound of the present invention evidences potential therapeutic utility in the treatment of hypertension, pulmonary disorders, e.g., asthma, congestive heart failure, cardiovascular shock, acute respiratory distress syndrome and the like.

The compound of the present invention can be administered in such oral dosage forms as tablets, capsules, pills, powders, granules, elixirs, or syrups. Likewise, administration may be effected intravascularly, intraperitoneally, subcutaneously, or intramuscularly using dosage forms known to those of ordinary skill in the pharmaceutical arts. In general, the preferred form of administration is oral. An effective but non-toxic amount of the compound is employed in treatment. The dosage regimen utilizing the present compound is selected in accordance with a variety of factors including the type, age, weight, sex, and medical condition of the patient; the severity of the condition to be ameliorated; and the route of administration. A physician of ordinary skill can readily determine and prescribe the effective amount of the drug required to prevent, treat or arrest the progress of the condition. Dosages of the compounds of the present invention, then used for the indicated cardiovascular, cardiopulmonary or respiratory effects will range gnerally between about 0.1 mg/kg/day to about 100 mg/kg/day and preferably between about 0.5 mg/kg/day to about 50 mg/kg/day. Advantageously, the compound of the present invention by reason of its long duration of action may be suitable for administration in a single daily dose. Of course, should it be necessary or desirable, the total daily dosage may be administered in equal divided doses three or four times daily.

In the pharmaceutical compositions and methods of the present invention, the active compound or a pharmaceutically acceptable salt thereof will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug component may be combined with any oral non-toxic pharmaceutically acceptable inert carrier such as lactose, starch, sucrose, cellulose, magnesium stearate, dicalcium phosphate, calcium sulfate, mannitol and the like; for oral administration in liquid form, the active drug component may be combined with any oral non-toxic pharmaceutically acceptable inert carrier such as ethanol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like.

The following non-limiting example further illustrates details for the preparation of the compound of the present invention. Those skilled in the art will readily understand and appreciate that known variations of the conditions and procedures in the following preparative method can be utilized. All temperatures are degrees Celcius unless otherwise noted. Melting points were determined on a Thomas-Hoover melting point apparatus and are uncorrected. Proton magnetic residence spectra were obtained in deuteriochloroform with tetramethylsilane as an internal standard using a Varian E-m 360 (60 MHz) spectrophotometer. Chemical shifts are reported in parts per million ($\delta$) downfield. Splitting patterns are designated as s, singlet; d, doublet; t, triplet; q quartet; and m, multiplet.

EXAMPLE 1

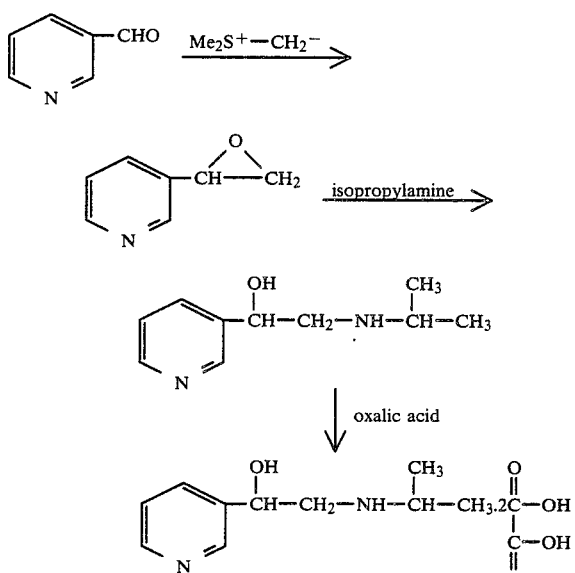

(A) 3-Oxiranyl pyridine

Dimethylsulfonium methylide ($Me_2S^+{-}CH_2^-$) was prepared by the addition of 2.20 trimethylsulfonium iodide (10 mmole, m.w. 220) in 9 ml of DMSO to a mixture of 240 mg NaH (10 mmole, m.w. 24) and 5 ml of DMSO in 5 ml of THF at 0° C. The foregoing mixture was stirred in ice water for 1 hour and 1.07 g of nicotine aldehyde (Aldrich Chem. Co.) (10 mmole, m.w. 107) in 5 ml of THF was added during 5 min. The ice water was removed and the mixture was allowed to stand for 1 hr. at room temperature. Then the mixture was cooled to 0° C. and 2 ml of water was added dropwise. THF was removed in vacuo and the organic material was extracted with 50 ml of ether. The ether extract was washed with $H_2O$ (30 ml×2), dried and filtered and the solvent removed. The resultant material was chromatographed on 50 g. of silica gel (70–230 mesh) using Skellysolve B-EtOAc (5:1) as the eluent. 3-Oxiranyl pyridine (300 mg) was separated from the starting material as a colorless oil (30% yield)

NMR ($\delta$, $CDCl_3$): 2.82 (d, d, 1H, J=5 and 3 Hz); 3.18 (d, d, 1H, J=5 and 4 Hz); 3.88 (d, d, 1H, J=3 and 3 Hz); 7.08–7.77 (m, 2H); 8.6 (m, 2H).

(B) α-[(1-Methylethylamino)methyl]-pyridinemethanol, oxalate salt 3-oxiranyl pyridine (300 mg, 2.5 mmole, m.w. 121) in 4 ml of methanol was cooled to 0° C. and 4 eq. of isopropylamine (300 mg, m.w. 59) added. The foregoing reaction mixture was stirred at room temperature overnight. Solvent was then removed in vacuo and the organic material was extracted with 40 ml of $Et_2O$.

The organic phase was washed with $H_2O$ (3x), dried and filtered. The solvent was removed in vacuo and the material obtained was chromatographed on 25 g of silica gel (70–230 mesh) using 80:19:1 $CH_2Cl_2$: $EtOAc$: $NH_4OH$ as the eluent. The pyridine methanol product (120 mg) was separated as a brown oil (55% yield).

NMR ($\delta$, $CDCl_3$): 1.06 (d, 6H, J=7 Hz); 2.6–3.1 (m, 3H); 4.75 (d, d, 1H, J=8 and 4 Hz); 7.22 (d, d, 1H, J=8 and 5 Hz); 7.75 (d, d, 1H, J=8 and 2 Hz); 8.33–8.66 (m, 2H).

To 120 mg of α-[(1-methylethylamino)methyl]-3-pyridine methanol in 5 ml of $Et_2O$ was added a saturated solution of oxalic acid in $Et_2O$ dropwise until the solution became slightly acidic. The resultant precipitate was recrystallized from MeOH to obtain 100 mg of the title oxalate salt as white needles (m.p. 165°–166°);

NMR ($\delta$, $D_2O$): 1.38 (d, 6H, J=6 Hz); 3.3–3.8 (m, 3H); 5.2 (d, d, 1H, J=7.5 and 5.5 Hz), 6.3 (s, 2H); 7.65 (d, d, 1H, J=8 and 5 Hz); 8.2 (d, d, 1H, J=8 and 2 Hz); 8.5–8.8 (m, 2H)

Calc'd. for $C_{10}H_{16}N_2O.2C_2H_2O_4$: C, 46.67; H, 5.59, N, 7.79. Found: C, 46.65; H, 5.61; N, 7.83.

PHARMACOLOGICAL EVALUATION

The compound of the present invention (Ex. 1B), referred to herein as test compound, was evaluated in accordance with the following in vivo and in vitro assay procedures to determine its pharmacological properties.

(A) Intravenous dose-response studies:

Six adult male spontaneously hypertensive rats were anesthetized with ether and instrumented with carotid artery and jugular vein catheters. The rats were allowed to recover from surgery and ether anesthesia for three to five hours. The test compound was administered intravenously in saline at doses of 0.1, 0.2, 0.7, 2, 7, and 20 mg/kg to give cumulative doses of 0.1, 0.3, 1, 3, 10, and 30 mg/kg. At the completion of these injections propranolol, a beta-adrenergic antagonist, was administered intravenously at a dose of 1 mg/kg and the injections of the test compound were repeated. The volume of each injection was 0.1 ml/100 grams of body weight. Mean arterial pressure and heart rate were measured via the carotid artery with a Statham pressure transducer and Gould physiological recorder. Results were analyzed using a paired t-test.

(B) Oral dosing studies:

Ten adult male spontaneously hypertensive rats were anesthetized with sodium pentobarbital and instrumented with a carotid arterial catheter. On the following day each rat was tethered in a plastic cage and arterial blood pressure and heart rate were monitored via the arterial catheter continuously for 72 hours. Each rat was dosed intragastrically with 100 mg/kg of the test compound each day for three days. A vehicle treated group (saline) of 10 rats was tested simultaneously. Differences in blood pressure between the treated and vehicle group were analyzed by the Kraskal-Wallis and Wilcoxon rank sum tests.

(C) Systemic hemodynamics:

Five adult male spontaneously hypertensive rats were anesthetized with sodium pentobarbital and instrumented with a femoral artery catheter for measuring arterial pressure and heart rate. The jugular vein was catheterized for injections and a thermocouple was placed in the aortic arch via the carotid artery for cardiac output measurement by the thermodilution technique. The trachea was cannulated and the rats breathed 100% oxygen. Control readings were taken and the test compound was injected in doses ranging from 0.1 to 30 mg/kg iv. After the 30 mg/kg dose, propranolol was injected iv at a dose of 1 mg/kg. Changes in hemodynamic parameters from control readings were analyzed by the paired t-test.

(D) Beta-adrenergic receptor binding:

Tissue preparation: Rat cerebellum plasma membranes were prepared by the method of U'Prichard et al, (J. Biol. Chem., 253, No. 14, pp. 5090–5102, 1978). Rat cerebellums were homogenized in 20 volumes of ice cold 50 mM Tris-HCl buffer (pH 7.4) with a Tekmar homogenizer. Crude plasma membranes were obtained by centrifugation at $45,000 \times$ g for 15 min with an intermediate rehomogenization in fresh buffer. The final pellets were resuspended in ten volumes of 50 mM buffer with 0.25M sucrose.

Binding Assay: Rat cerebellum plasma membrane preparations (10 mg wet weight per ml in a volume of one ml) were incubated with 1 nM [$^3$H] DHA in buffer, 1 mM catechol and 0.01% ascorbic acid, either in the presence or absence of various amounts of test substance at room temperature for 20 minutes. Bound and free radioligand were separated by addition of 3.5 ml buffer (0° C.) followed by rapid filtration through Whatman GF/B glass fiber filter. The filter was then washed rapidly with three 3.5 ml buffer (3X). Specific binding was defined as the amount of the [$^3$H]DHA bound in the absence of competing ligand minus the amount bound in the presence of 10 uM ($\pm$) propranolol (nonspecific binding). Competition experiments were carried out with at least 5 concentrations of the displacing agent in duplicate. IC$_{50}$ (inhibitory concentration $-50\%$) values were calculated from the displacement data after logit-log transformation with least squares linear regression.

RESULTS

In the foregoing tests the compound of Example 1B, reduced mean arterial pressure by 25% in conscious spontaneously hypertensive rats (SHR) at a calculated intravenous dose of 37 mg/kg. Daily oral dosing at 100 mg/kg for 3 days in the conscious SHR lowered mean arterial pressure by 39 mmHg at 3–4 hours after dosing and pressure remained reduced for 6–10 hours. Heart rate was elevated by 114 beats/min. Propranolol, 1 mg/kg iv, attenuated the hypertension and tachycardia produced by the compound of the invention, suggesting that the compound of the invention produces its cardiovascular effects by activating $\beta$-adrenergic receptors.

The test compound inhibited the -$\beta$-adrenergic receptor binding of tritiated dihydroalprenolol in rat cerebellum cortex with an IC$_{50}$ of $3.9 \times 10^{-5}$M further indicating the $\beta$-adrenergic agonist activity of the present compound. In the pentobarbital anesthetized spontaneously hypertensive rat, the compound of the invention increased cardiac output from 72 to 92 ml/min and decreased total peripheral resistance from 3 to 1.1 units. Propranolol again reversed these hemodynamic effects.

The above results reflect that the compound of the present invention is a long-acting orally active cardiovascular agent which produces its hypotensive effects by systemic vasodilation via $\beta$-adrenergic receptor activation.

While the invention has been described and illustrated with reference to certain preferred embodiments thereof, those skilled in the art will appreciate that various changes, modifications, and substitutions can be made therein without departing from the spirit of the invention. For example, effective dosages other than the preferred ranges set forth hereinabove may be applicable as a consequence of variations in the responsiveness of the mammal treated, severity of condition treated, dosage related adverse effects, if any, observed and analogous considerations. Likewise, the specific pharmacological responses observed may vary depending upon the particular active compounds selected or whether different active compounds are used in combination or in the presence of suitable pharmaceutical carriers, as well as the type of formulation and mode of administration employed, and such expected variations or differences in results are contemplated in accordance with the objects and practices of the present invention. It is intended, therefore, that the invention be limited only by the scope of the claims which follow.

What is claimed is:

1. A compound of the formula

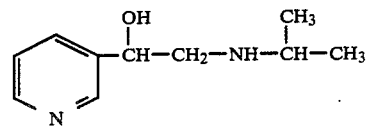

which is $\alpha$[(1-methylethylamino)methyl]-3-pyridinemethanol and pharmaceutically acceptable salts thereof.

2. A compound according to claim 1 wherein said pharmaceutically acceptable salt is an oxalate salt.

3. A pharmaceutical composition comprising a $\beta$-adrenergic receptor agonist effective amount of a compound according to claim 1 in combination with a pharmaceutically acceptable carrier.

4. A composition according to claim 3 wherein said composition is formulated in dosage unit form.

5. A composition according to claim 4 wherein said dosage unit form is adapted for oral administration.

6. A method of increasing cardiac output or promoting an anti-hypertensive or peripheral vasodilating effect in a mammal in need thereof comprising administering thereto a non-toxic therapeutically effective amount of a compound according to claim 1.

7. A method according to claim 6 wherein said compound is administered in combination with a pharmaceutically acceptable carrier.

8. A method according to claim 6 wherein said compound is administered as an oxalate salt thereof.

9. A method according claim 6 wherein said compound is administered orally.

10. A method of promoting a β-adrenergic receptor agonist effect in a mammal in need thereof comprising administering thereto a non-toxic agonist effective amount of a compound according to claim 1.

11. A method according to claim 10 wherein said β-adrenergic receptor agonist effect is a hypotensive effect.

* * * * *